(12) United States Patent
Oberle

(10) Patent No.: US 8,277,477 B2
(45) Date of Patent: Oct. 2, 2012

(54) MECHANICALLY DEPLOYABLE UPPER AIRWAY STENT

(76) Inventor: Paul Oberle, Ballwin, MO (US)

( * ) Notice: Subject to any disclaimer, the term of this patent is extended or adjusted under 35 U.S.C. 154(b) by 561 days.

(21) Appl. No.: 12/390,173

(22) Filed: Feb. 20, 2009

(65) Prior Publication Data

US 2010/0217302 A1  Aug. 26, 2010

(51) Int. Cl.
*A61M 29/00* (2006.01)
*A61F 2/04* (2006.01)

(52) U.S. Cl. .................. 606/191; 623/23.64; 623/23.65; 623/23.7

(58) Field of Classification Search ........ 623/1.15–1.16, 623/9, 23.64–23.7; 606/191, 196, 199, 41, 606/200; 604/96.01, 104, 108; 128/207.18
See application file for complete search history.

(56) References Cited

U.S. PATENT DOCUMENTS

| | | | |
|---|---|---|---|
| 2,525,183 A | 10/1950 | Robison | |
| 4,457,756 A | 7/1984 | Kern et al. | |
| 5,139,510 A | 8/1992 | Goldsmith, III et al. | |
| 5,282,817 A | 2/1994 | Hoogeboom et al. | |
| 5,643,309 A * | 7/1997 | Myler et al. | 623/1.15 |
| 6,159,158 A | 12/2000 | Lowe | |
| 6,183,493 B1 | 2/2001 | Zammit | |
| 6,248,128 B1 * | 6/2001 | Berry et al. | 623/1.17 |
| 6,328,753 B1 | 12/2001 | Zammit | |
| 6,394,093 B1 | 5/2002 | Lethi | |
| 6,450,989 B2 | 9/2002 | Dubrul et al. | |
| 6,814,749 B2 | 11/2004 | Cox et al. | |
| 2005/0027247 A1 | 2/2005 | Carrison et al. | |
| 2005/0124849 A1 | 6/2005 | Barbut et al. | |
| 2005/0240147 A1 | 10/2005 | Makower et al. | |
| 2006/0004323 A1 | 1/2006 | Chang et al. | |
| 2006/0149310 A1 | 7/2006 | Becker | |
| 2007/0129751 A1 | 6/2007 | Muni et al. | |

FOREIGN PATENT DOCUMENTS

EP  0 418 391 A1  6/1989

OTHER PUBLICATIONS

U.S. Appl. No. 12/150,174, filed Apr. 25, 2008.
Office action dated Jan. 11, 2011 from U.S. Appl. No. 12/150,174.
Office Action dated Dec. 6, 2011 from co-pending U.S. Appl. No. 12/150,174.

* cited by examiner

*Primary Examiner* — Thomas J Sweet
*Assistant Examiner* — Yashita Sharma
(74) *Attorney, Agent, or Firm* — Evans & Dixon, LLC; Don V. Kelly

(57) ABSTRACT

A mechanically deployable upper airway stent is disclosed along with a method of using same. The stent comprises a central tube having an inner chamber and openings on its surface. A linkage rod is housed within the central tube and is provided with branched spokes that pass through the openings. In the un-deployed state the branched spokes are contained within the central tube. Deployed spokes are preferably aligned in groupings along the central tube. The outer ends of the spokes of each grouping connect to a rib. The un-deployed stent is inserted into the nasal passageway and positioned relative to occluding anatomic structures. Upon deployment, the ribs along with web members extending between the ribs move outwardly from the central tube and press upon the tissues of the pharyngeal cavity. Spaces between the extended spokes permit the passage of air along the stent and maintain airway patency.

13 Claims, 14 Drawing Sheets

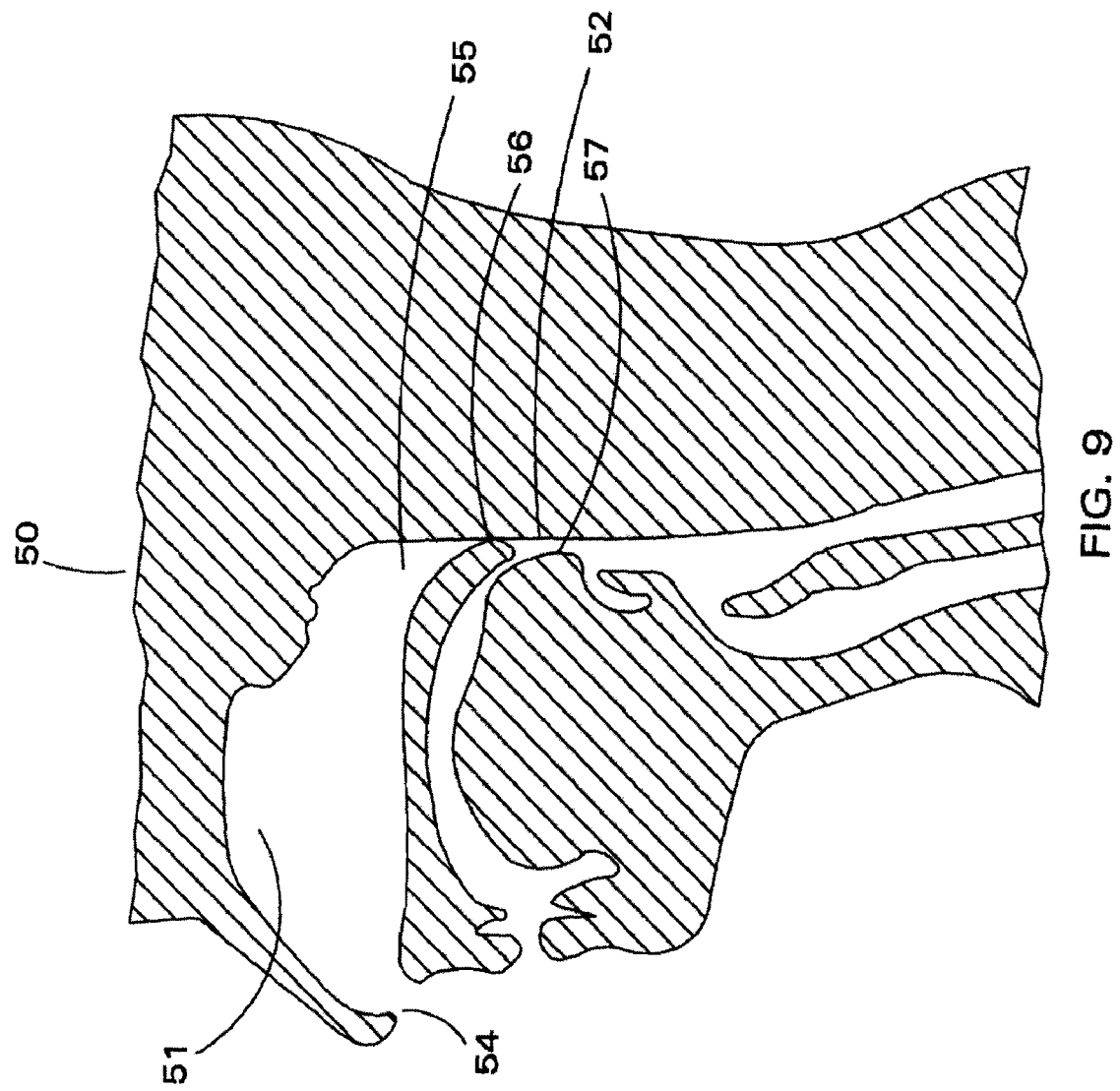

MECHANICALLY DEPLOYABLE UPPER AIRWAY STENT

CROSS REFERENCE TO RELATED APPLICATION

Not applicable.

STATEMENT REGARDING FEDERALLY SPONSORED RESEARCH OR DEVELOPMENT

Not applicable.

SEQUENCE LISTING TABLE OR COMPUTER PROGRAM OR COMPACT DISC

Not applicable.

FIELD OF THE INVENTION

This invention relates generally to methods and devices for treating pharyngeal obstructions and maintaining pharyngeal airway patency. More specifically, this invention relates to an improved method and apparatus for treating sleep apnea and breathing disorders caused by undesirable inflammation, configuration, growth or motility of the structures of the nasopharynx or oropharynx.

BACKGROUND OF THE INVENTION

An apnea is a period of time during which breathing stops or is markedly reduced. In simplified medical terms, an apnea occurs when a person stops breathing for 10 seconds or more. Apneas usually occur during sleep. Sleep apnea is a disorder characterized by a reduction or cessation of breathing airflow during sleep. A reduction or cessation of airflow during sleep causes a resultant drop in blood oxygen level. This reduced blood oxygen level is detected by the brain, which sends out a signal to the body to wake up and take a breath. Consequently, when an apnea occurs, sleep is disrupted. Sometimes this means the person wakes up completely, but sometimes this can mean the person comes out of a deep level of sleep and into a more shallow level of sleep.

There are two basic types of sleep apnea: central sleep apnea and obstructive sleep apnea. Of the two types, obstructive sleep apnea is more common. Central sleep apnea occurs when the brain does not send the signal to the muscles to take a breath, and there is no muscular effort to take a breath. Obstructive sleep apnea occurs when the brain sends the signal to the muscles and the muscles make an effort to take a breath, but they are unsuccessful because the airway becomes obstructed and prevents the flow of air. In some instances, a patient may have both forms of sleep apnea, in which case the patient is considered to have "mixed apnea."

Obstructive sleep apnea is estimated to affect about 4% of men and 2% of women. The prevalence of obstructive sleep apnea can be correlated to obesity within a population, as obesity exacerbates obstructive sleep apnea. Some studies suggest that among obese patients, upwards of 70% have obstructive sleep apnea. Obstructive sleep apnea can cause or exacerbate existing conditions of high blood pressure, stroke, extreme daytime sleepiness, ischemic heart disease, insomnia and mood disorders. In addition, patients with obstructive sleep apnea who receive sedation, analgesia or anesthesia for diagnostic or therapeutic procedures are at increased risk for perioperative complications.

During sleep in a person not having obstructive sleep apnea, air passes through the nasal passages, behind the palate, uvula, and tongue base, through the throat muscles, between the vocal cords and into the lungs. With obstructive sleep apnea, undesirable growth, configuration, swelling or motility of the nasal passages, palate, tongue, and pharyngeal tissues can all contribute to narrowing of the airway. In some cases, people with obstructive sleep apnea have an airway that is more narrow than normal, usually at the base of the tongue and palate. When lying flat, the palate is normally above the air passage. As shown in FIG. 9, in an apneic patient, when the pharyngeal muscles relax, the palate can fall backwards. Similarly, as shown in FIG. 9, relaxation of the genioglossus muscle during sleep allows the base of the tongue to fall backwards. These events can obstruct the airway. In many case the tissues of the airway are often sucked together by the negative pressure of air traveling into the lungs. This tissue action can exacerbate the degree of obstruction because the harder the chest tries to pull air in, the greater the negative pressure, and the more the tissues of the airway are sealed together.

The treatment of obstructive sleep apnea may be either surgical or nonsurgical. Surgical options for sleep apnea, however, may involve painful recoveries and extended time off from work to heal. Surgical options are also dependent on an individual's specific anatomy and severity of sleep apnea. Surgical options for treatment of obstructive sleep apnea include nasal airway surgery, palate implants, uvulopalatopharyngoplasty, tongue reduction, genioglossus advancement, hyoid suspension, maxillomandibular procedures, tracheostomy and bariatric surgery. Because these surgeries carry risk and offer no guarantee of improvement, most patients with obstructive sleep apnea go through a regimen of non-surgical treatments before considering surgery. Non-surgical treatments for obstructive sleep apnea include postural sleeping changes, dental appliances, medications (decongestants and steroid sprays) and use of CPAP (continuous positive airway pressure) devices.

CPAP is probably the best, non-surgical treatment for obstructive sleep apnea. A CPAP machine blows heated, humidified air through a short tube into a mask affixed to the patient's face. CPAP uses air pressure to hold airway tissues open during sleep. By delivering air through a nasal or face mask under pressure, as the patient breathes, the gentle pressure holds the nose, palate, and throat tissues open. The effectiveness of CPAP requires that the mask must be worn snugly to prevent the leakage of air. This is often difficult because of the discomfort engendered by masks. Critically, if the mask does not fit correctly, the efficacy of CPAP drops significantly. Also, when employing a CPAP machine, it is important to use the lowest possible pressure that will keep the airway open during sleep. However, different pressures may be needed for different positions or levels of sleep. These pressure levels, however, must be determined in a clinical setting or require an "auto-titrating" feature on the CPAP machine. Hence another disadvantage of CPAP is that it is not always easy to use. Studies show that only 60% of people with CPAP machines actually use them. When actual use time is measured, only 45% of those patients that actually use the machines use them more than 4 hours per night. Of those people who begin a CPAP regimen, 25 to 50 per cent will stop using CPAP despite the persistence of symptoms.

Due to the compliance issues attendant to CPAP treatment modalities, other methods of maintaining airway patency have been proposed. In this regard, use of a nasopharyngeal tube has been proposed to maintain airway patency. Though originally designed for placement by a physician, some prior art airway maintenance devices are intended for nightly use at home by the patient. For instance U.S. Pat. No. 6,328,753 discloses a folded tube intended for insertion into a patient's nostril and into the nasal passage way. Using a tube, however, to maintain, biologic passageway patency has certain disadvantages. First, the tube must be made of a sufficiently rigid material to enable insertion into the oropharynx. The fact that the tube is constructed of such material and that the tube has a large surface area increases the possibility of irritating contact with body tissues. Similarly, the large surface area of the tube can interfere with the natural secretory functions of surrounding tissues and sinuses of the nasal cavities. Accordingly, a need exists for an improved patient-usable, upper airway patency device that eliminates or minimizes the deficits of prior art devices.

SUMMARY OF THE INVENTION

The invention herein is directed to a mechanically deployable upper airway stent that maintains airway patency and a method of using same. The invention can be used to treat obstructions in the nasopharynx and oropharynx, as well as sleep apnea, in both the home and perioperative setting. As a home-use device, the stent can be placed into position by a patient before going to sleep. In the perioperative setting, medical personnel can utilize the device both during and after administration of sedatives, analgesics or anesthetics to reduce complications in apneic patients.

In a preferred embodiment the present invention stent comprises an elongate central tube having a lumen, a first (proximal) end and a second (distal) end. The central tube houses a linkage rod. The linkage rod has first and second ends respectively corresponding to the first and second ends of the central tube. The linkage rod is axially disposed within the length of the housing. The linkage rod is adapted for reciprocating axial movement within the housing. The first end of the central tube has means to control the axial movement of the linkage rod within the central tube. In the depicted preferred embodiment, the first end of the linkage rod projects out from the first end of the central tube to allow the user to apply spoke-deploying or spoke-withdrawing force to the rod. In the preferred embodiment, a pushing motion imparts the spoke-deploying force and a pulling motion imparts the spoke-withdrawing force.

The present invention stent further includes a plurality of spokes connected to the linkage rod and extending out through the openings disposed on the central tube. In the preferred embodiment the spokes are formed as integral branched extensions of the linkage rod. However, the spokes may be pivotally attached to the linkage rod by conventional mechanical means. Each spoke has an inner end, an outer end and is connected to the linkage rod at its inner end. Preferably, in the un-deployed state, the majority of each spoke resides within the housing of the central tube with the outer end of the spoke extending through an opening of the central tube. The stent includes a plurality of ribs. Each rib has a proximal end, a distal end, a first side and a second side. Each rib is connected to two or more spokes at their outer ends. Further, each of the two or more spokes connected to each rib is serially located at different axial positions along the central tube. The two or more spokes connected to each rib form a grouping of spokes. In the shown preferred embodiment, optional web members extend from the sides of adjacent ribs.

In a preferred embodiment, the plurality of spokes extend out through the central tube such that they form groupings of axially (lengthwise) or helically aligned spokes. Each grouping comprises at least two spokes. The spokes of each grouping are connected at their outer end to a perimeter rib. The present invention stent therefore comprises a plurality of ribs that preferably extend longitudinally along or helically about the central tube. Each rib has two ends. One end is the proximal end, which of the two rib ends is nearest the first (proximal) end of the central tube. The other end is the distal end, which of the two rib ends is nearest the second (distal) end of the central tube. Each rib has a preferred length at least that of the length of the grouping of spokes to which it is attached. In a preferred embodiment, an aligning lead extends from the distal end of each rib to the distal end of the central tube. Also in the preferred embodiment, an aligning lead extends from the proximal end of each rib to the proximal end of the central tube. It is desirable that one or more web members extend from each side of the rib to an adjacent rib. Preferably each web member contacts the rib at a point where a spoke meets the rib.

To deploy the preferred embodiment stent, the linkage rod is moved axially in a distal direction within the housing of the central tube. The movement of the linkage rod causes the spokes to move through the openings of the central tube and project radially outward from the tube. In a preferred embodiment, each spoke is made of a sufficiently rigid material such that when the stent is deployed the spokes are sufficiently strong to prevent collapse of pharyngeal tissues. As a spoke moves radially outward, each rib (along with attached web members) moves outwardly away from the central tube. In the preferred embodiment the fully deployed spoke will extend outwardly at an angle approximately normal (70-110 degrees) to the central tube. When all spokes have been deployed and are radially extended, spaces between adjacent deployed spokes permit the easy passage of air along the length of the stent. The inter-spoke spaces of the preferred embodiment stent are wedge-shaped.

In use, the collapsed (un-deployed) stent of the present invention is inserted through a naris and into the nasal passageway. The stent is typically fully inserted when the distal end of the stent is proximal to the soft palate structures of the nasophraynx. In cases where the obstruction is due to lingual collapse, the stent may be inserted into position in the oropharynx where its distal end is proximal to and presses against the base of the tongue. In the full insertion mode a sufficient length of the proximal end of the stent extends out through the naris to permit manipulation and deployment of the stent. Once fully inserted, a portion of the stent is proximal to the anatomic structure or structures of the pharynx (nasopharynx and/or oropharynx) exhibiting undesirable inflammation, configuration, growth or motility. The stent can then be deployed and fixed into position. The proximal end of the central tube is provided with gripping means such as knurlments to enhance positioning and removal of the stent. In its deployed state, the perimeter ribs and web members of the stent press outwardly against the tissues of the pharynx prohibiting their collapse or incursion into the airway. By virtue of the inter-spoke spaces, air may freely pass through the nasal passageway into the pharynx.

BRIEF DESCRIPTION OF THE DRAWINGS

FIG. 9 is a cross section view of the upper airway in a patient with apnea causing obstructions in the nasopharynx and oropharynx.

DETAILED DESCRIPTION OF THE INVENTION

The present invention relates to a mechanically deployable pharyngeal stent and method of using same. In its un-deployed state, the stent has a reduced diametric profile and is insertable into the nasal passageway via one of the nares. Once fully inserted and positioned, the stent is deployed. Deploying the stent causes radially movable spokes bearing perimeter ribs to move outwardly from the stent such that the ribs and their optional adjoining web members press against the tissues of the pharyngeal cavity that define the patient airway. The pressing force from the stent restricts tissue swelling, incursion or motility and therefore prevents the structures of the nasopharynx or oropharynx from collapsing or intruding into the airway. Inter-spoke spaces allow the flow of air along the length of the stent and result in airway patency.

For purposes of description herein, the term "proximal" shall refer to that portion of the stent or component thereof that is situated closest to the manipulating hand of a user. The term "distal" shall refer to that portion of the disclosed stent or a component thereof that is situated or moved, further away from the manipulating hand of the user. A preferred embodiment present invention pharyngeal stent is shown in the deployed state in FIGS. 1-5. Stent 1 comprises central tube 2 having lumen 3. Central tube 2 is made from a biocompatible material that is: (a) rigid enough to allow the tube to be pushed through a curving biologic passageway, such as the upper airway; and (b) flexible enough to follow the contours of the passageway without damaging surrounding tissues. Suitable materials include, for example, nylon, PVC, polyurethane, polyethylene, and polypropylene.

Figure 1:
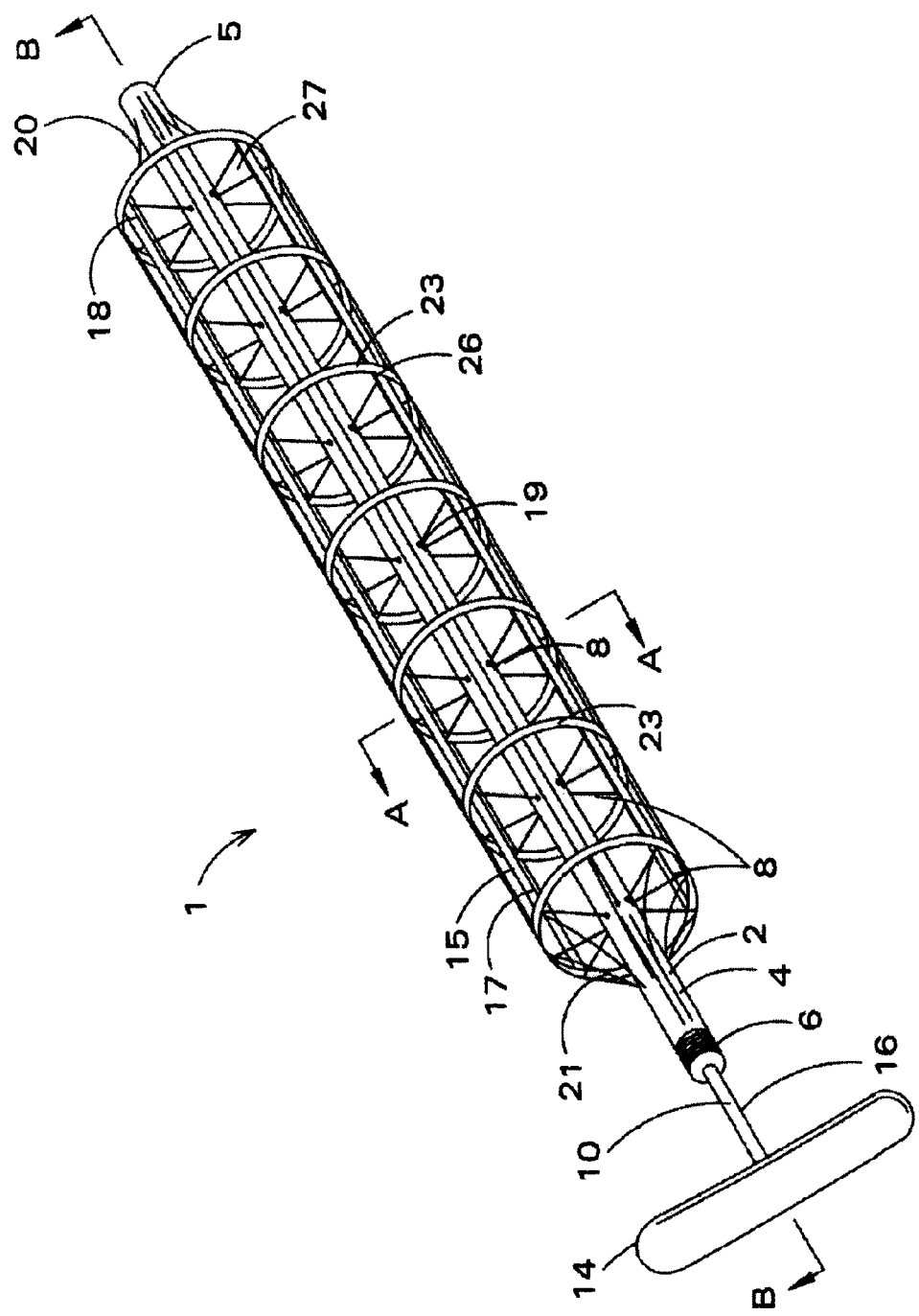
FIG. 1 is a perspective view of a preferred embodiment upper airway stent of the present invention in the deployed state.
Figure 2:
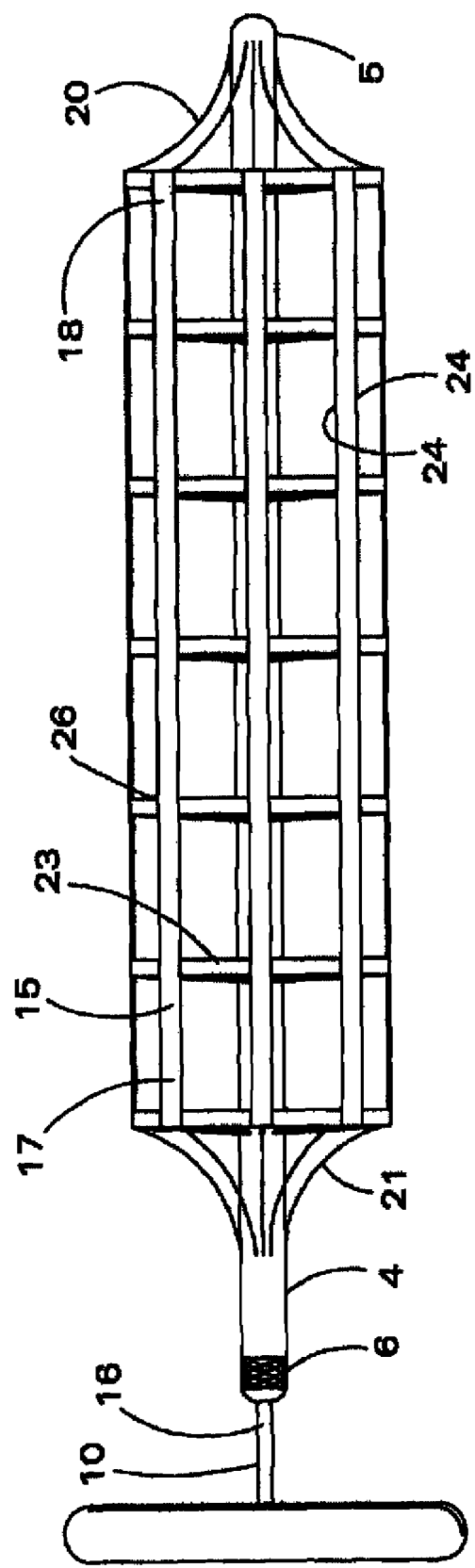
FIG. 2 is a side elevation view of a preferred embodiment upper airway stent of the present invention in the deployed state.
Figure 3:
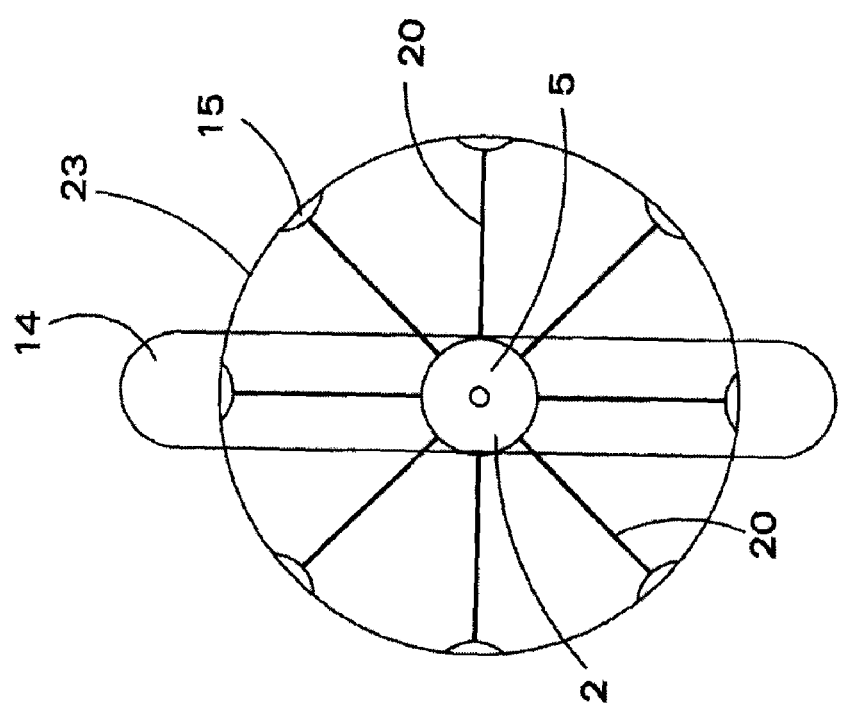
FIG. 3 is a distal end elevation view of a preferred embodiment upper airway stent of the present invention in the deployed state.
Figure 4:
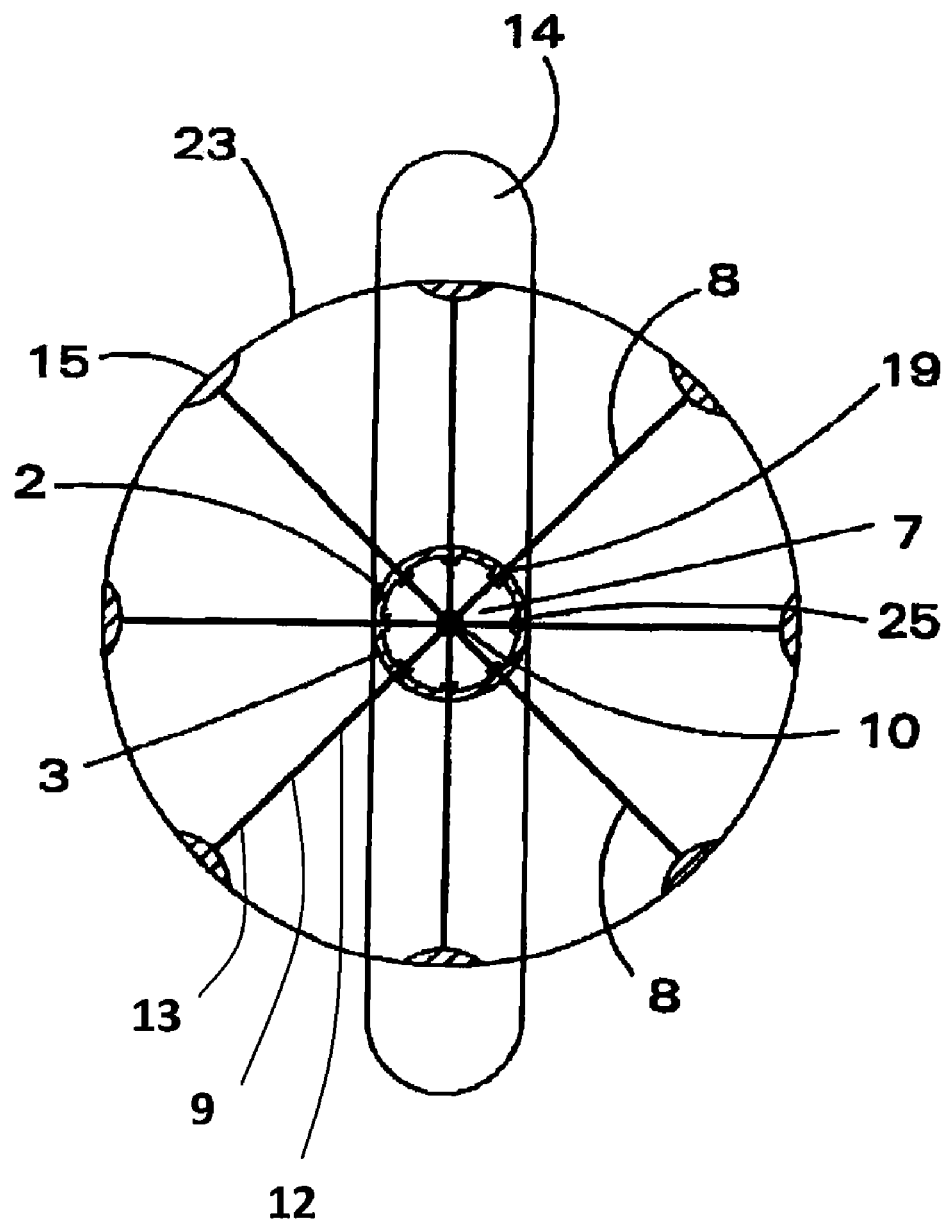
FIG. 4 is a cross section view taken along line A-A of FIG. 1 of a preferred embodiment upper airway stent of the present invention in the deployed state.

Central tube 2 has a proximal end 4 and distal end 5. Distal end 5 of tube 2 is preferably closed and is shaped for non-traumatic insertion into the upper airway. Proximal end 4 includes gripping means 6. Exemplary gripping means include knurlments. As best seen in FIG. 4, lumen 3 of tube 2 defines a central inner chamber 7. Inner chamber 7 houses linkage rod 10. Linkage rod 10 is axially disposed within tube 2. The first end of the central tube includes means to control the axial movement of the linkage rod within the central tube. In this regard and in the preferred embodiment, first end 16 of rod 10 projects out of proximal end 4 and also includes gripping means 14, preferably in the form of a handle, such that linkage rod 10 operates as a push rod. Examples of other axial motion control means could include threaded drive mechanisms, worm gears or telescope gearing. A plurality of spokes 8 connect to linkage rod 10. In the preferred embodiment spokes 8 are integrally formed as flexible branches of linkage rod 10. When formed in this fashion, linkage rod 10 and spokes 8 can be molded as a single unit from the same material. Alternatively, spokes 8 could be separate structures pivotally connected to linkage rod 10 by known mechanical means. Each spoke passes through an associated opening 19 on central tube 2 and comprises a shaft 9, an inner end 12 and an outer end 13.

In the preferred embodiment of the present invention, when the stent is in the un-deployed state, each spoke 8 is mostly contained within central tube 2. To permit this configuration, openings 19 of central tube 2 includes guide sleeves 25 to direct the movement of its associated spoke 8. In the un-deployed state the portion of each spoke contained within tube 2 lies along linkage rod 10. In this state, the outer end 13 of each spoke 8 is positioned near opening 19.

Figure 5:
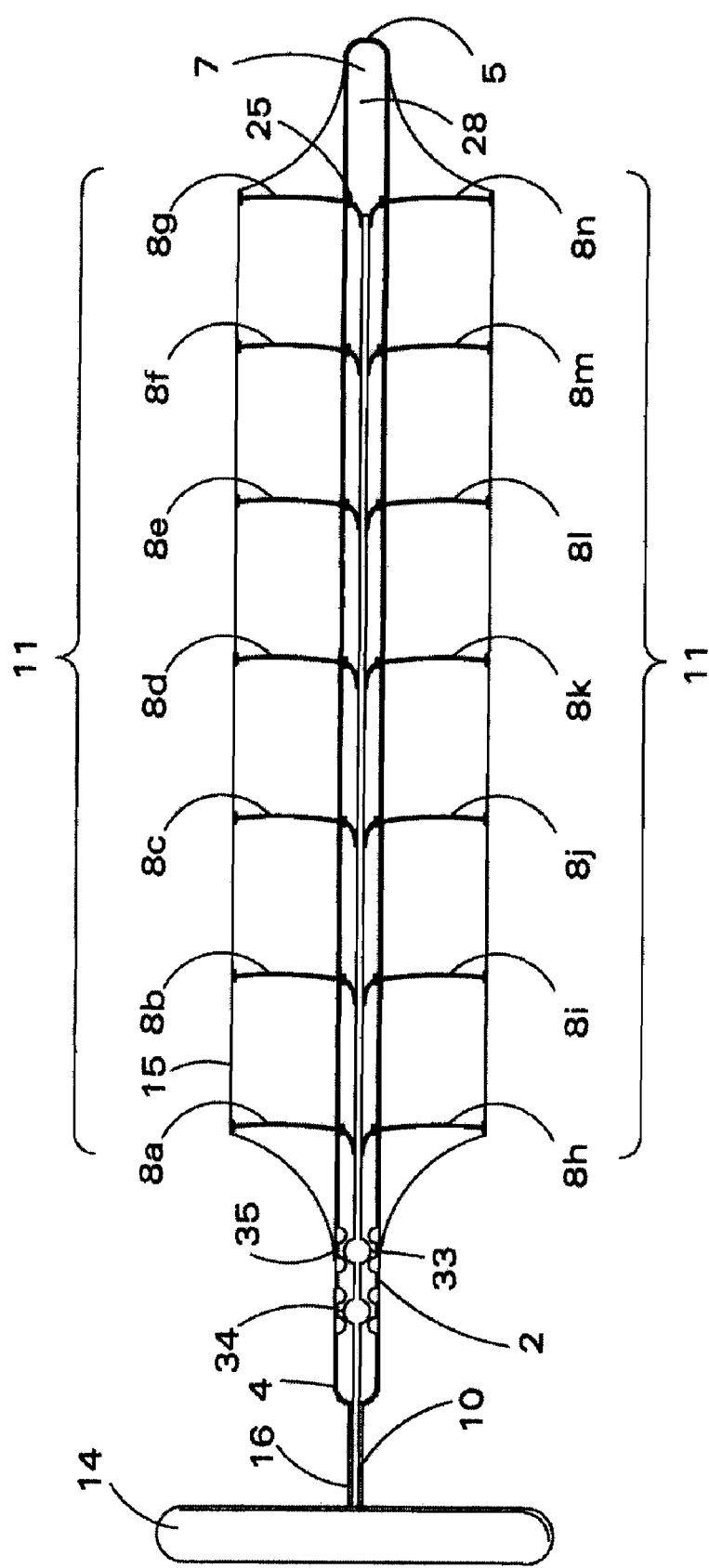
FIG. 5 is a cross section view taken along line B-B of FIG. 1 of a preferred embodiment upper airway stent of the present invention in the deployed state.

In a preferred embodiment, openings 19 on central tube 2 are arranged such that when the plurality of spokes 8 are deployed, they will form one or more groupings 11 of axially or helically aligned spokes 8. Each grouping 11 comprises at least two spokes 8. The figures disclose a preferred embodiment stent having spokes that are axially (length-wise) aligned along central tube 2. As best seen in FIG. 5, two spoke groupings of seven spokes (one group consisting of spokes 8a-8g and the other group consisting of spokes 8h-8n) are identified. In the depicted preferred embodiment, two or more spokes 8 of each grouping 11 are connected at their outer end 13 to a rib 15 extending longitudinally (axially) along central tube 2 and running the length of the respective grouping 11. In this depicted embodiment and in the un-deployed state, spokes 8 are positioned within central tube 2, preferably lying in an approximately longitudinal direction along the central tube. In an alternate embodiment, spokes 8 (and correspondingly, openings 19) may be helically aligned in groupings 11 such that the spokes of each grouping are connected at their outer end 13 to a rib 15 that extends helically about central tube 2.

Stent 1 comprises a plurality of ribs 15. Each rib 15 has a proximal end 17 and distal end 18. In a preferred embodiment, a distal aligning lead 20 extends from distal end 18 of at least one rib 15 to distal end 5 of tube 2 and a proximal aligning lead 21 extends from the proximal end 17 of at least one rib 15 to the proximal end 4 of central tube 2. One or more web members 23 may optionally extend from a side 24 of a perimeter rib 15 to an adjacent perimeter rib 15 to maintain the alignment of spokes 8 and their groupings 11. Preferably each web member 23 contacts the perimeter rib 15 at the point 26 where a spoke 8 meets the perimeter rib 15. In a preferred embodiment web members are made of a biocompatible flexible plastic or rubber compound.

Figure 6:
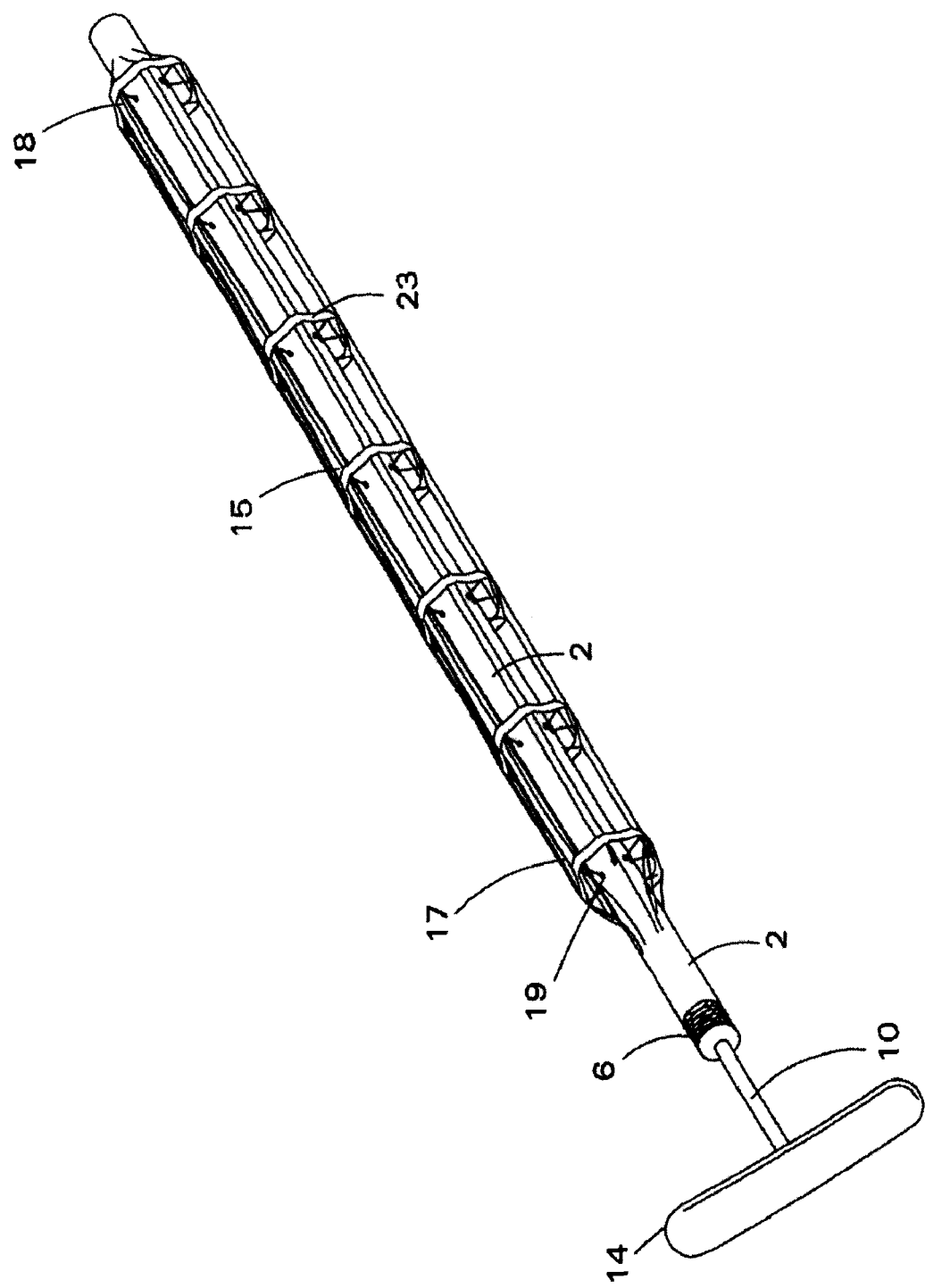
FIG. 6 is a perspective view of a preferred embodiment upper airway stent of the present invention in the un-deployed state.
Figure 7:
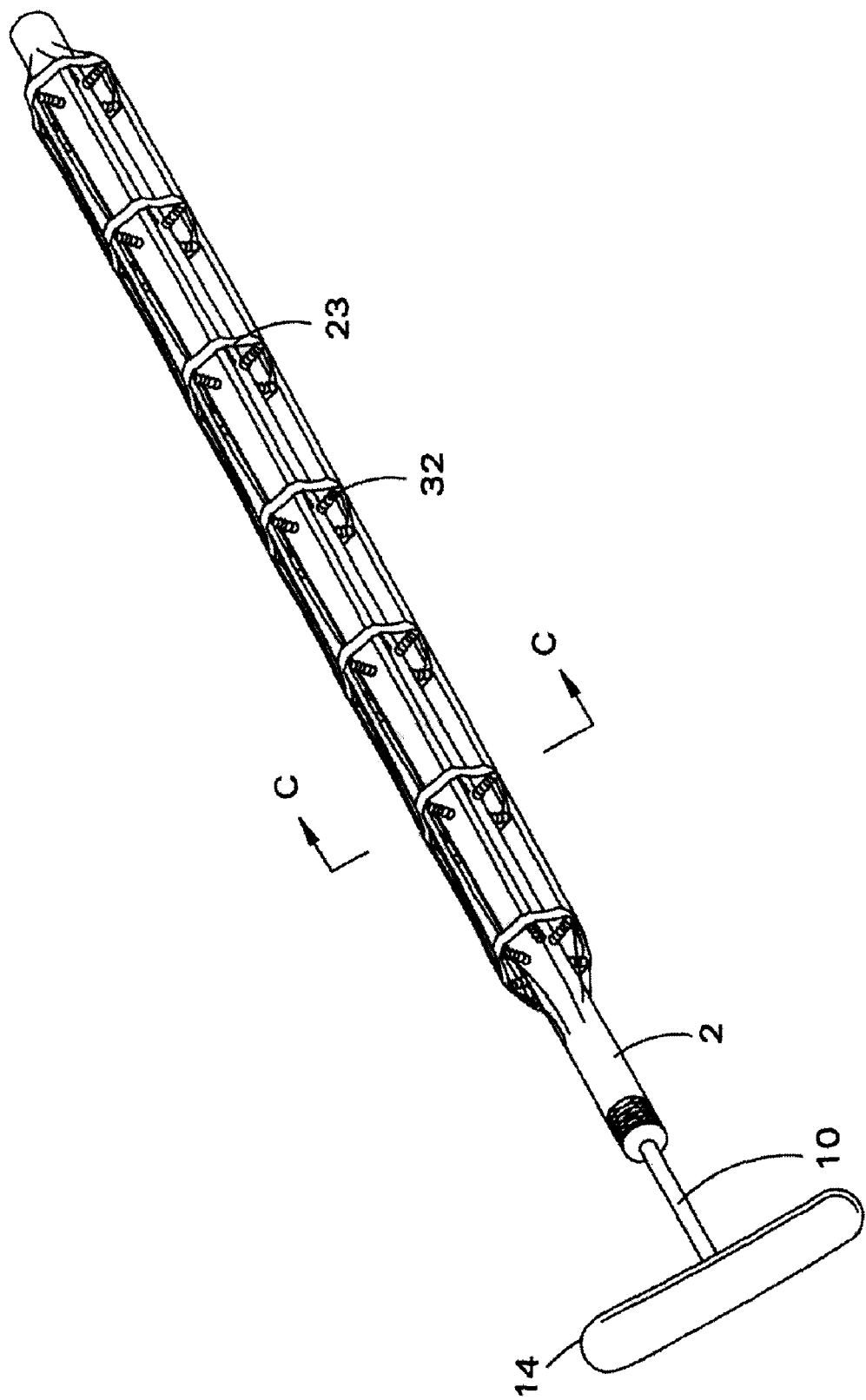
FIG. 7 is a perspective view of an alternate embodiment upper airway stent of the present invention in the un-deployed state, the stent having accordiated sheaths that cover the spokes.
Figure 8A:
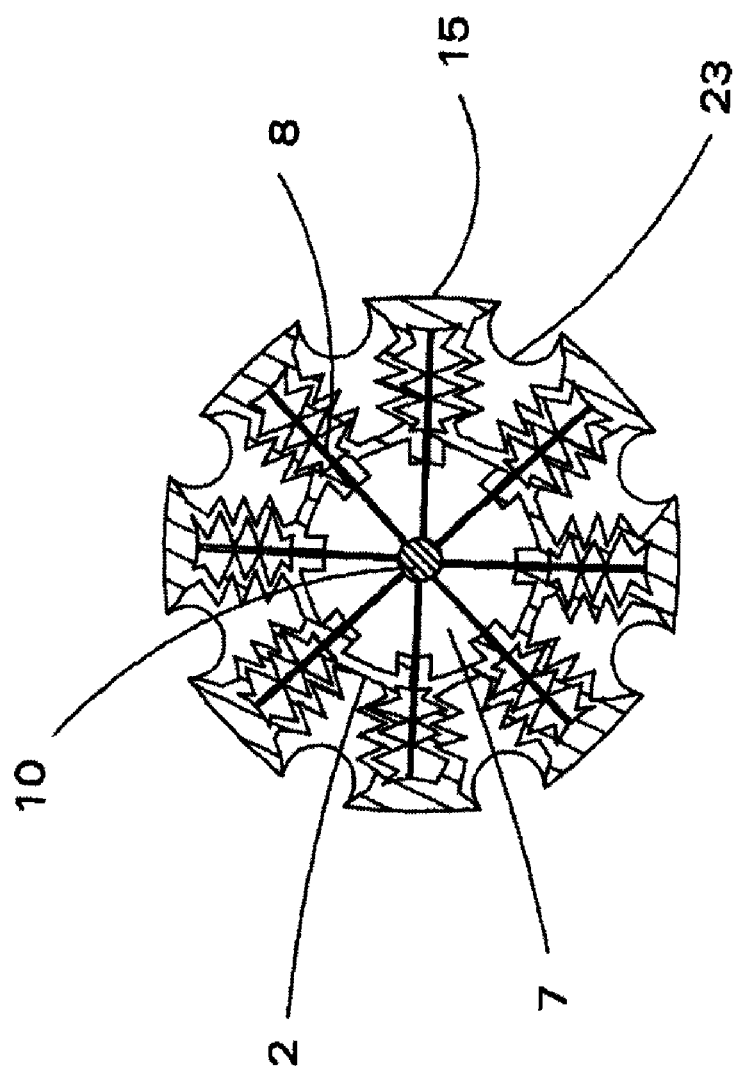
FIGS. 8a-c are cross section views taken along line C-C of the alternate embodiment upper airway stent of FIG. 7 depicting the stent transitioning from the un-deployed state to the deployed state.
Figure 8B:
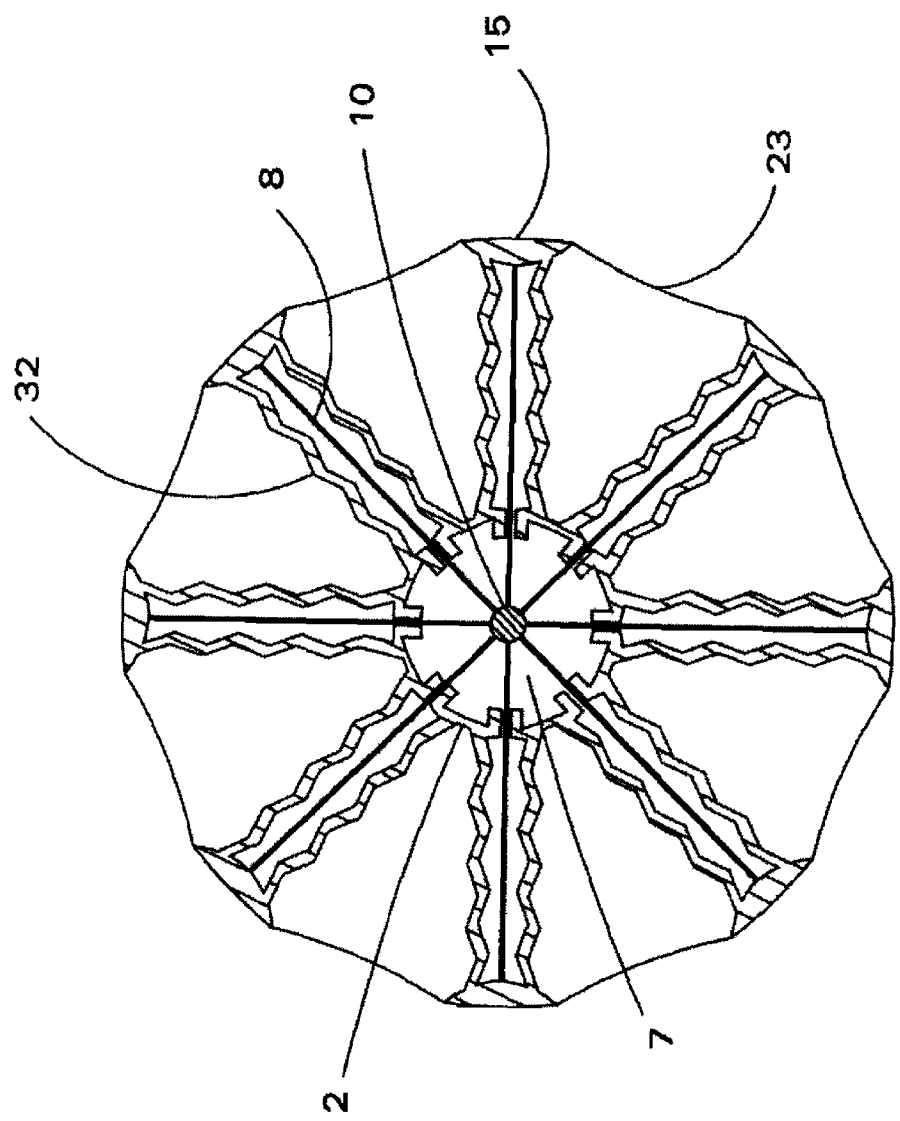
Figure 8C:
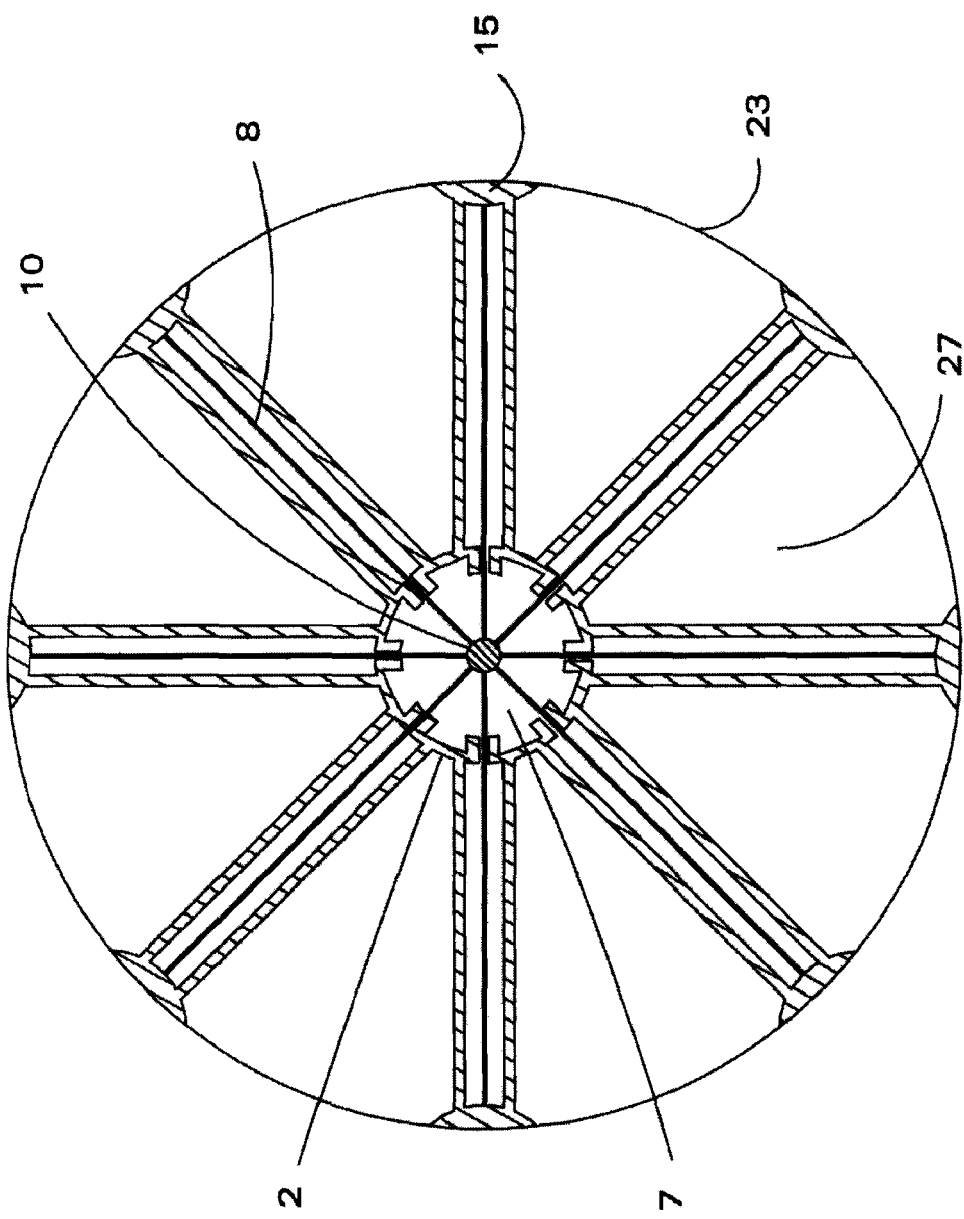
Figure 10:
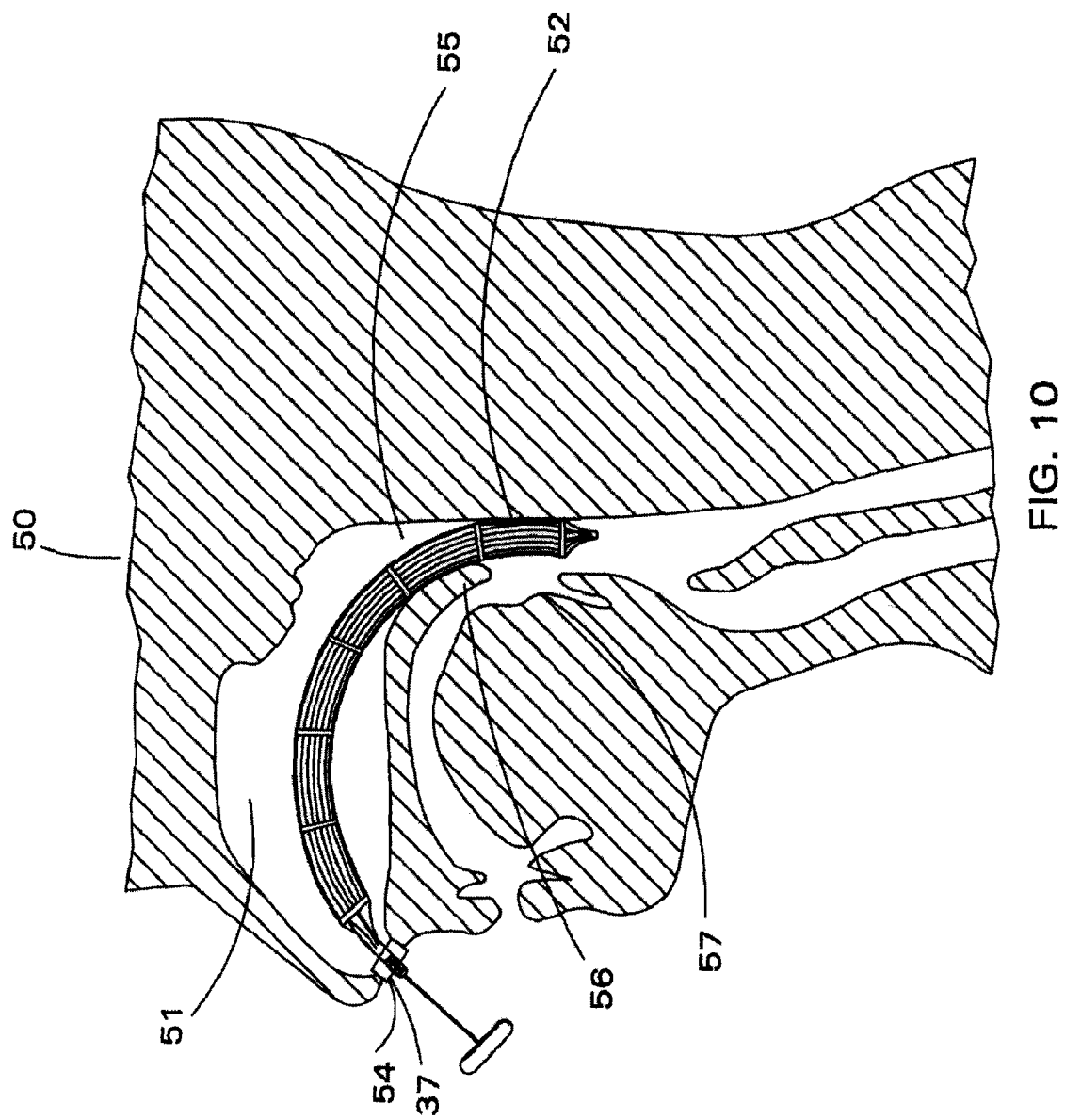
FIG. 10 is a cross section view of the upper airway in which a preferred embodiment stent of the present invention is inserted in its un-deployed state.

Each spoke 8 is made of a flexible but sufficiently rigid material such that when the linkage rod is pushed into the central tube 2, spokes 8 are caused to move through openings 19 and project radially outward from tube 2. For stents having axially aligned spoke groupings, the un-deployed spokes reside within central tube 2 and lie longitudinally or approximately longitudinally on rod 10. Depending upon the chosen embodiment of the stent, the un-deployed spokes will preferably extend in an approximate longitudinal direction or helical direction within central tube 2. For helically arranged groupings, the optimum deploying force to the linkage rod would include imparting axial movement plus a twisting movement that will align the spoke inner ends 12 with openings 19. Suitable spoke material includes PVC, polyurethane, polypropylene or polyethylene. As shown in FIGS. 6 and 10, in the un-deployed state stent 1 is easily insertable through a patient's nasal passageway into the oropharynx. In the preferred embodiment, when linkage rod 10 is moved distally within tube 2, each spoke 8 moves from its housed position to a radially extending position, approximately normal to central tube 2. Ribs 15 are disposed upon the outer ends 13 of spokes 8. Hence, when all spokes 8 have deployed and are radially extended, ribs 15 and web members 23 are located outwardly remote from central tube 2. As noted in the figures, in the embodiment shown, linkage rod 10 does not fully occupy the length of central tube 2. Central tube 2 includes space 28 to permit the travel of distal end 16 of linkage rod 10 when rod 10 is moved in reciprocating fashion inside tube 2. In a preferred embodiment, ribs 15 are made of a biocompatible, soft but flexibly rigid material such as PVC, polyurethane, polypropylene or polyethylene to reduce irritation of the pharyngeal tissues. Inter-spoke spaces 27 are created when spokes 8 are fully deployed. Inter-spoke spaces 27, which in the preferred embodiment are wedge-shaped, are located between adjacent deployed spokes 8 and permit the easy passage of air along the length of the stent 1.

As shown in FIGS. 7, 8a, 8b, and 8c, in an alternate embodiment, central tube 2 can include spoke sheaths 32 attached to central tube 2. Each spoke sheath 32 is attached to an opening 19. Spoke sheaths 32 seal the inside of tube 2 from bodily fluids that could interfere with the deploying action of the spokes. Spoke sheaths 32 are preferably accordiated and are formed from a soft elastic material such as rubber, urethane or plastic. In addition, so that a sheath 32 follows the movement of its associated spoke 8 as the spoke moves in and out of the central tube 2, it is preferred that the outer end 13 of each spoke be connected to the top 36 of each sheath 32.

FIG. 9 shows the structures of the upper airway. As seen in FIG. 9, upper airway 50 includes naris 54, nasal passageway 51, nasopharynx 55, oropharynx 52, soft palate 56 and the area behind tongue base 57. More specifically, FIG. 9 shows the upper airway of a patient suffering from sleep apnea due to prolapse of the soft palate 56 and tongue 57. This condition, or any other obstruction of the pharyngeal cavity caused by growth, configuration, swelling or motility of the tissues, can be remedied by the method of using the present invention stent described herein. As shown in FIG. 10, un-deployed stent 1 of the present invention is inserted through the naris 54 and into the nasal passageway 51. Stent 1 is typically fully inserted when distal end 5 is pushed proximal to or just beyond the soft palate structures 56 above the oropharynx 52. In cases where the obstruction is due to lingual collapse, the stent may be inserted into position where its distal end is proximal to and presses against the base 57 of the tongue. When properly inserted, a portion of the device is proximal to the anatomic structure having the undesirable inflammation, configuration, growth or motility. When properly inserted in accordance with the apnea-causing condition, proximal end 16 (via handle 14) of rod 10 is grasped while simultaneously grasping proximal end 4 of tube 2. End 16 of rod 10 is then pushed into tube 2 (toward the user's face) while maintaining tube 2 in place in the upper airway. Applying such force to handle 14 causes linkage rod 10 to move relative to tube 2 and push spokes 8 out through directional guide sleeve 25 and openings 19. The translation of such force to spoke inner ends 12 also causes spokes 8 to become erect and project away from tube 2. In the full insertion mode, proximal end 4 of tube 2 and proximal end 16 of rod 10 (with handle 14) extend out through naris 54 leaving a sufficient length of the stent for manipulation and deployment.

The present invention stent can include structure to assist in maintaining the stent in the collapsed (reduced diameter) state and in the deployed state. As shown in FIG. 5, the proximal end of rod 10 is provided with a position bead 33 adapted to friction fit within either of two spaced-apart detents 34, 35 formed in the interior wall of the proximal end 4 of central tube 2. In the un-deployed or inserting state, bead 33 will rest within detent 34. In the deployed state, bead 33 will rest within detent 35. Stent 1 could also comprise a split sleeve surrounding the stent and holding spokes 8 within central tube 2. The sleeved stent could be inserted into the upper airway and the sleeve withdrawn out through the naris, leaving the stent in place. With the sleeve withdrawn, spokes 8 can be radially extended via reciprocating motion of linkage rod 10. As with prior art devices, the mechanically deployable upper airway stent of the present invention can comprise an outer surface lubricant and anesthetic (either on the sleeve or stent itself) to aid in insertion and patient comfort.

Figure 11:
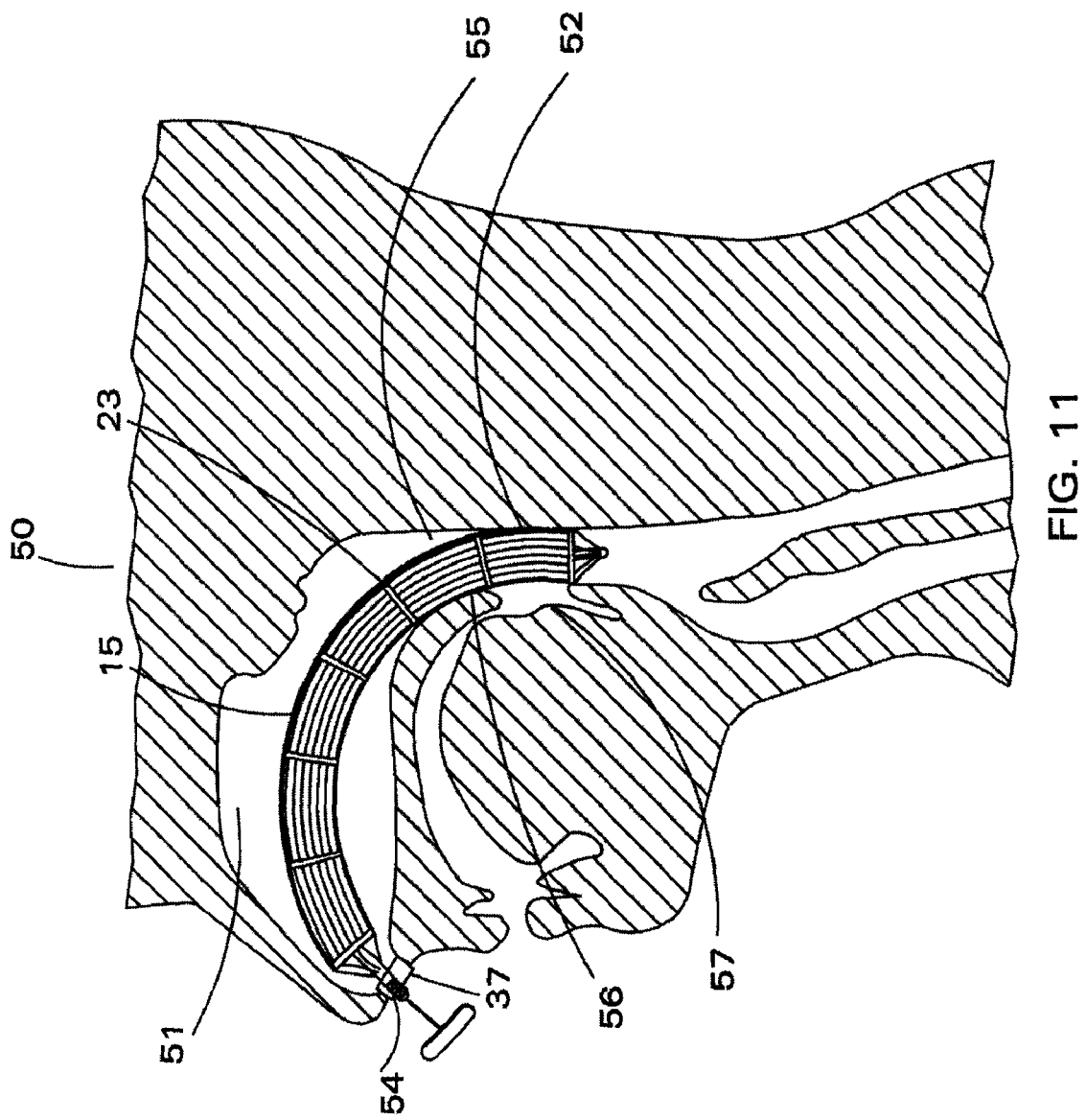
FIG. 11 is a cross section view of the upper airway in which a preferred embodiment stent of the present invention is in place in its deployed state, eliminating the apnea causing obstructions of FIG. 9.

Once inserted to the proper location in the pharynx the stent can be deployed. Rod 10 could include preferred gripping means such as handle 14. FIG. 11 is a cross section view of an upper airway in which a preferred embodiment stent of the present invention is inserted in its deployed state. As shown in FIG. 11, deployed spokes 8 of preferred embodiment stent 1 radially project from central tube 2. By virtue of the deployment of spokes 8, perimeter ribs 15 and web members 23 are disposed outwardly remote from central tube 2 and press against the tissues of the nasopharynx 55 or oropharynx 52. In particular, formerly prolapsed soft palate 56 shown in FIG. 9 is now held in place by ribs 15, web members 23 or both. By virtue of inter-spoke spaces 27, air may freely pass along stent 1 and through nasal passageway 51 into the oropharynx 52 resulting in airway patency. Additionally, the pressing action of perimeter ribs 15, web members 23 or both against the tissues of airway 51, holds stent 1 in place. Thus, in contrast to the prior art pharyngeal patency devices, the present invention is designed for friction or compression fit within the nasopharynx or oropharynx. However, as added protection against aspiration of stent 1, stent 1 can include a fenestrated cuff 37 at proximal end 4 of tube 2. As compared to prior art devices, the scaffold-like, open structure of the stent allows for the reasonably unimpeded flow of secretions from the sinuses of the nasopharyngeal cavity.

The present invention stent is sized to allow comfortable insertion into the nasal passage. In this regard, the device may have an un-deployed diametric profile that will range practically from 5 to 10 millimeters in diameter. In the deployed state the diametric profile will range practically from 10 to 20 millimeters in diameter. Stent 1 can have a practical length that can range from 10 to 16 centimeters. Length and width wilt vary to accommodate varying pharyngeal dimensions among different patients. When stent 1 is properly inserted and sized, distal end 5 should lie in the oropharynx 52, preferably proximal to or just beyond the soft palate 56 or tongue base 57 depending upon the patient's condition. When inserted thusly, this leaves several centimeters of the proximal end 4 projecting from the nostril for manipulation and inflation. As with other prior art patency devices, the present invention inflatable pharyngeal stent can be adapted to be used in conjunction with other airway obstruction treatments such as CPAP.

Figure 12:
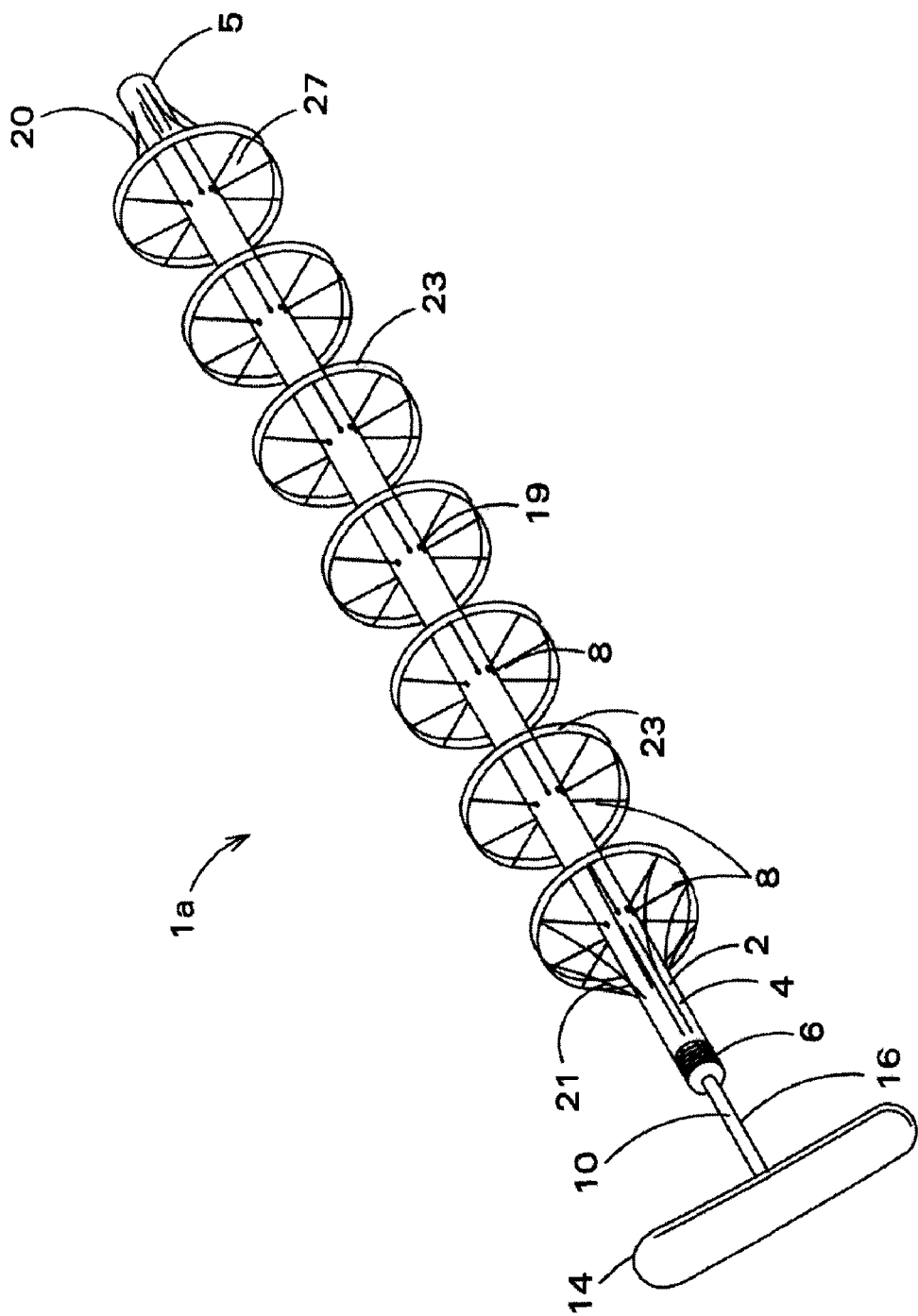
FIG. 12 is a perspective view of an alternative embodiment stent of the present invention.

A simpler alternate embodiment stent 1a could comprise a plurality of similarly axially-distanced spoke groupings. Each grouping comprises a plurality of spokes 8 emanating from central tube 2 out of openings 19 and attached to the same web member 23. Hence, the spokes of each grouping project through openings located at the same or substantially the same axial distance along central tube 2. This alternate embodiment is shown in FIG. 12. Each set of spokes 8 that emanate from a group of similarly axially-distanced openings would constitute a spoke grouping. This alternate embodiment stent thus comprises a plurality of axially-distanced spoke groupings. Each spoke grouping comprising a plurality of spokes that: are connected to the linkage rod; are radially disposed about the linkage rod; and project out through a plurality of openings located at the same or substantially the same axial distance along the central tube. This alternate embodiment stent would omit rib structures 15 and simply comprise one or more web members 23 extending between adjacent spokes 8 of each grouping 11. Web members 23 would be connected to spokes 8 at outer ends 13. In a preferred embodiment web members are made of a biocompatible flexible plastic or rubber compound. The spokes of this alternate embodiment could include sheaths, including the depicted accordiated sheaths.

While particular embodiments of the present invention have been illustrated and described herein, the present invention is not limited to such illustrations and descriptions. The embodiments shown and described are merely preferred embodiments. It is apparent that changes and modifications may be incorporated and embodied as part of the present invention within the scope of the following claims. For example, the number of spokes 8 can be varied depending upon strength and flexibility demands. Similarly, inter-spoke spacings 27 can be numbered and individually sized to permit ancillary tubes (not shown) to be introduced for feeding, supplying oxygen or for suction. The stent could also be optionally configured such that the spokes are deployed by pulling force applied to the linkage rod instead of the described pushing force.

What is claimed is:

1. A stent for treating anatomic occlusions of the nasopharynx and oropharynx, the stent comprising:
   a central tube having an inner chamber, a first end, a second end and a plurality of openings on its surface;
   a linkage rod having a first end and a second end, the linkage rod being axially disposed within the inner chamber and adapted for axial movement within the inner chamber;
   means to control the axial movement of the linkage rod positioned near the first end of the central tube;
   a plurality of spokes, each spoke connected to the linkage rod and projecting out through an opening on the central tube;
   each spoke having an inner end, an outer end and being connected to the linkage rod at its inner end;
   a plurality of ribs, each rib being connected to two or more spokes at their outer ends; and
   each of the two or more spokes connected to a rib being serially located at different axial positions along the linkage rod.

2. The stent of claim 1 wherein the two or more spokes connected to a rib form a grouping of spokes axially aligned on the central tube.

3. The stent of claim 1 wherein the two or more spokes connected to a rib form a grouping of spokes helically aligned on the central tube.

4. The stent of claim 1 wherein each rib has a first side and a second side; and one or more of the ribs have one or more web members extending from each side to an adjacent rib.

5. The stent of claim 1 wherein each rib has a proximal end and a distal end; and at least one rib has an aligning lead that extends from the distal end of the rib to the distal end of the central tube.

6. The stent of claim 1 wherein each rib has a proximal end and a distal end; and at least one rib has an aligning lead that extends from the proximal end of the rib to the proximal end of the central tube.

7. The stent of claim 1 wherein one or more of the spokes are integral branched extensions of the linkage rod.

8. The stent of claim 1 wherein one or more spokes are mechanically attached to the linkage rod.

9. The stent of claim 1, wherein the stent upon deployment further comprises wedge-shaped spaces between adjacent spokes.

10. The stent of claim 1 wherein the plurality of spokes lie along the linkage rod when the device is in its un-deployed state and upon deployment of the stent each spoke moves through an opening on the central tube until it extends radially outward from the central tube at an angle approximately normal to the central tube.

11. The stent of claim 2 wherein the one or more spokes connected to a rib that form a grouping extend in an approximate longitudinal direction along the linkage rod when the device is an un-deployed state.

12. The stent of claim 3 wherein the one or more spokes connected to a rib that form a grouping extend in an approximate longitudinal direction along the linkage rod when the device is an un-deployed state.

13. The stent of claim 1 wherein one or more spokes is contained within a sheath.

* * * * *